United States Patent
Lukacsovich et al.

(10) Patent No.: US 7,026,525 B1
(45) Date of Patent: Apr. 11, 2006

(54) VECTOR FOR GENE TRAP, AND A METHOD FOR GENE TRAPPING BY USING THE VECTOR

(75) Inventors: Tamas Lukacsovich, Tokyo (JP); Zoltan Asztalos, Tokyo (JP); Daisuke Yamamoto, Tokyo (JP); Wakae Awano, Kanagawa (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/700,843

(22) PCT Filed: May 21, 1999

(86) PCT No.: PCT/JP99/02683

§ 371 (c)(1),
(2), (4) Date: Feb. 2, 2001

(87) PCT Pub. No.: WO99/61604

PCT Pub. Date: Dec. 2, 1999

(30) Foreign Application Priority Data

May 22, 1998 (JP) ................................. 10/141952

(51) Int. Cl.
*A01K 67/033* (2006.01)
*C12N 15/09* (2006.01)
*C12N 15/85* (2006.01)

(52) U.S. Cl. ........................... 800/25; 800/21; 800/22; 435/320.1; 435/455

(58) Field of Classification Search ............. 435/320.1, 435/325, 455; 800/13, 21, 22
See application file for complete search history.

(56) References Cited

U.S. PATENT DOCUMENTS 6,136,566 A * 10/2000 Sand et al. ................ 435/69.7

OTHER PUBLICATIONS

Thummel et al . Gene 74:445-456, 1988.*
Pirrotta et al . Biotechnology Vectors a survey of molecular cloning vectors and their uses, ed. RL Rodriguez et al. vol. 1, 1988, pp. 437-456, Buttersworths Press, Boston.*
Gustafson K, Boulianne GL .Genome 1996 39(1):174-82.*
Brand et al., "Targeted gene expression as a means of altering cell fates and generating dombinant phenotypes," Development 118: 410-415, 1993.*

* cited by examiner

*Primary Examiner*—Scott D. Priebe
(74) *Attorney, Agent, or Firm*—Wenderoth, Lind & Ponack, L.L.P.

(57) ABSTRACT

The present application provides a vector for trapping an unknown gene of Drosophila melanogaster, which is a recombinant plasmid comprising the following nucleotide sequences in this order: an artificial consensus splicing acceptor site; a synthetic "stop/start" sequence; a reporter gene; a drug resistance gene; a gene responsible for a detectable phenotype of the Drosophila melanogaster; and a synthetic splicing donor site. The present application also provide a method for trapping an unknown gene of Drosophila melanogaster by using the vector.

13 Claims, 7 Drawing Sheets

Precise splicing of Gal4 and mini-white genes from Gene Trap vector into anterior open gene 5'P end of vector; splice acceptor site/stop-start seq.;Gal4 gene......mini-white gene/splice donor site; 3'P end of GT vector
..........tttgcgatgcaagtctctttctcttacag/gtcgaattgtgtgatccaatgaagt..........agcttcgccgcgcgcaagcgtacag/gtaagtagcgcgcgcatacgtaagttaatg.........

anterior open cDNA    exon 1                                  exon 2
cagtacgtaaccaccagtgcacagtggagcaaacag/ataacaccgcttaaaagcaattccagtggcttccac anterior open exon 1 - Gal4 fusion cDNA
cagtacgtaaccaccagtgcacagtggagcaaacag/gtcgaattgtgtgatccaatgaagt mini-white - anterior open exon 2 fusion cDNA
agcttcgccgcgcgcaagcgtacag/ataacaccgcttaaaagcaattccagtggcttccac

Fig. 7

Gal4 expression patterns revealed by UAS-lacZ reporter construct.

A — line 77 adult brain
B — line 49 larval brain
C — line 6 larval brain

VECTOR FOR GENE TRAP, AND A METHOD FOR GENE TRAPPING BY USING THE VECTOR

BACKGROUND OF THE INVENTION

1. Field of the Invention

The present invention relates to a new vector system to facilitate the cloning and functional analysis of new genes of a fly, *Drosophila melanogaster*, and a method for gene trapping with the vector system.

2. Description of the Related Art

There are numerous examples for application of gene trapping methods in wide range of living organisms including maize and mouse (Gossler et al,. Science, 244:463–465, 1989).

With respect to tools for gene trapping, the application of different types of enhancer trap P-element vectors (Wilson et al., Genes & Development, 3:1301–1313, 1989) for cloning and analyzing trapped genes, as well their use for mosaic analysis with the help of the Gal4/UAS transcription activator system has proven fruitful. However, sometimes the expression pattern of the Gal4 or other reporter gene of the vector construct is affected by enhancers belonging to more than one gene. Similarly, in some cases it is difficult to determine whether the enhancer trap insertion effects the function of one or more of the neighboring genes.

These circumstances altogether with the fact that in some cases the mutant phenotype could be attributed to the changed expression of a gene with its nearest exon located more than 30 kB apart from the insertion site, can lead in unfortunate cases to an ordeal when it's time to clone and analyze the affected gene.

One object of this application is to provide a vector system that includes specifically designed artificial regulatory sequences as well as selection methods for easy screening of positive recombinant lines. More especially, this application intends to provide a vector system of this invention offering much easier and faster cloning opportunities of the affected gene, compared to the widely used enhancer trap P-element vectors. Another object of this application is to provide easier detection method possibilities of the successful trapping events and much higher chance to get more characteristic ("functional") expression patterns of the reporter gene because in the contrary with much of the cases with enhancer trap lines, when using the vector system of this invention, the reporter gene expression is influenced only by a single endogenous transcription unit and effects only the expression of the very same gene.

SUMMARY OF INVENTION

The first invention of this application is a vector for trapping an unknown gene of *Drosophila melanogaster*, which is a recombinant plasmid comprising the following nucleotide sequences in this order:
  an artificial consensus splicing acceptor site;
  a synthetic "stop/start" sequence;
  a reporter gene;
  a drug resistance gene;
  a gene responsible for a detectable phenotype of the *Drosophila melanogaster*; and
  a synthetic splicing donor site.

One embodiment of the first invention is that the recombinant plasmid is derived from pCasper3.

Other embodiments of the first invention are that the reporter gene is the Gal4 gene, Gal4 DNA binding domain-P53 fusion gene or the Gal4-firefly luciferase fusion gene.

Further embodiment of this first invention is that the gene responsible for a detectable phenotype of the *Drosophila melanogaster* is mini-white gene.

More further embodiment of the first invention is that the drug resistance gene is neomycin-phosphotranspherase gene and its promoter is a heatshock promoter.

The second invention of this application is a method for trapping an unknown gene of *Drosophila melanogaster* by using a vector which is a recombinant plasmid comprising the following nucleotide sequences in this order:
  an artificial consensus splicing acceptor site;
  a synthetic "stop/start" sequence;
  a reporter gene;
  a drug resistance gene;
  a gene responsible for a detectable phenotype of the *Drosophila melanogaster*; and
  a synthetic splicing donor site,
    which method comprises the steps of:
    (a) introducing the vector into the genome of a white minus fly;
    (b) selecting primary transformants resistant to a drug;
    (c) crossing the primary transformants with a transposase source strain to force the vector to jump into other locations;
    (d) selecting secondary transformants by picking up the flies having strong eye color,
    (e) crossing the secondary transformants with UAS (Upstream Activator Sequence)-luciferase harboring strain and measuring the reporter gene expression of the resultant flies; and
    (f) identifying the trapped gene by cloning and sequencing the cDNAs fused to the reporter gene and the gene responsible for a detectable phenotype of the fly.

The third invention of this application is a method for trapping an unknown gene of *Drosophila melanogaster* by using a vector A which is a recombinant plasmid comprising the following nucleotide sequences in this order:
  an artificial consensus splicing acceptor site;
  a synthetic "stop/start" sequence;
  Gal4 DNA binding domain-P53 fusion gene as a reporter gene;
  a drug resistance gene;
  a gene responsible for a detectable phenotype of the *Drosophila melanogaster*; and
  a synthetic splicing donor site, and a vector B derived from pCasperhs, which has the heatshock promoter directed Gal4 activator domain-large T antigen fusion gene within polycloning site of the pCasperhs,
    which method comprises the steps of:
    (a) introducing each of the vectors A and B into the genomes of separate white minus flies;
    (b) selecting primary transformants for the vector A which are resistant to the drug, and selecting primary transformants for the vector B which have an eye color;
    (c) crossing the primary transformants for the vector A with a transposase source strain to force the vector to jump into other locations;
    (d) selecting secondary transformants for the vector A by picking up the flies having strong eye color;
    (e) crossing the secondary transformants with the primary transformants for the vector B to obtain flies harboring both the vectors A and B;

(f) crossing the flies obtained in the step (e) with an UAS-luciferase harboring fly strain and measuring the reporter gene expression of the resultant flies after a heatshock treatment; and (g) identifying the trapped gene by cloning and sequencing the cDNAs fused to the reporter gene and the gene responsible for a detectable phenotype of the fly.

Embodiments of the second and third inventions are corresponded to the embodiments of the first invention, and they will be more precisely described in the following description.

BRIEF DESCRIPTION OF THE DRAWINGS

The 5'P end of vector, splice acceptor site of this figure is represented by SEQ ID No: 2. The stop-start seq., Gal4 gene of this figure is represented by SEQ ID No: 3. The miniwhite gene of this figure is represented by SEQ ID No: 4. The splice donor site 3'P end of GT vector of this figure is represented by SEQ ID No: 5. The anterior open cDNA exon 1 of this figure is represented by SEQ ID No: 6. The anterior open cDNA exon 2 of this figure is represented by SEQ ID No:7. The anterior open exon 1-Gal 4 fusion cDNA is represented by the combination of SEQ ID No: 6 and 3 in this order. The mini-white-anterior open exon 2 fusion cDNA is represented by the combination of SEQ ID No: 4 and 7 in this order.

DESCRIPTION OF THE PREFERRED EMBODIMENTS

A vector construct of the first invention, for example, can be based on the commonly used, P-element transformation vector, pCasper3 (Pirotta, Vectors: A survey of molecular cloning vectors and their uses, eds. Rodriguez, R. L. & Denhardt, D. T., Butterworths, Boston. 437–456, 1998) and the convenient Gal4-UAS expression system (Brand and Perrimon, Development, 118:401–415, 1993).

A promoterless Gal4 gene preceded by an artificial consensus splicing acceptor site and a synthetic "stop/start" sequence to govern the read through translation coming from upstream exon(s) of the trapped gene into the proper reading frame of Gal4 was inserted into the polycloning site of pCasper3.

The removal of the whole 3' UTR (untranslated region) sequence of the mini-white gene and replacement by an artificial splicing donor site resulted in a truncated gene without its own poly-adenylation site.

Without a successful gene trapping event this truncated mini-white gene was not expected to confer any eye color, therefore in this invention a heatshock promoter directed neomycin-phosphotransferase (hs-neo) gene for helping selection of primary transformants by antibiotic feeding has been inserted.

Figure 1:
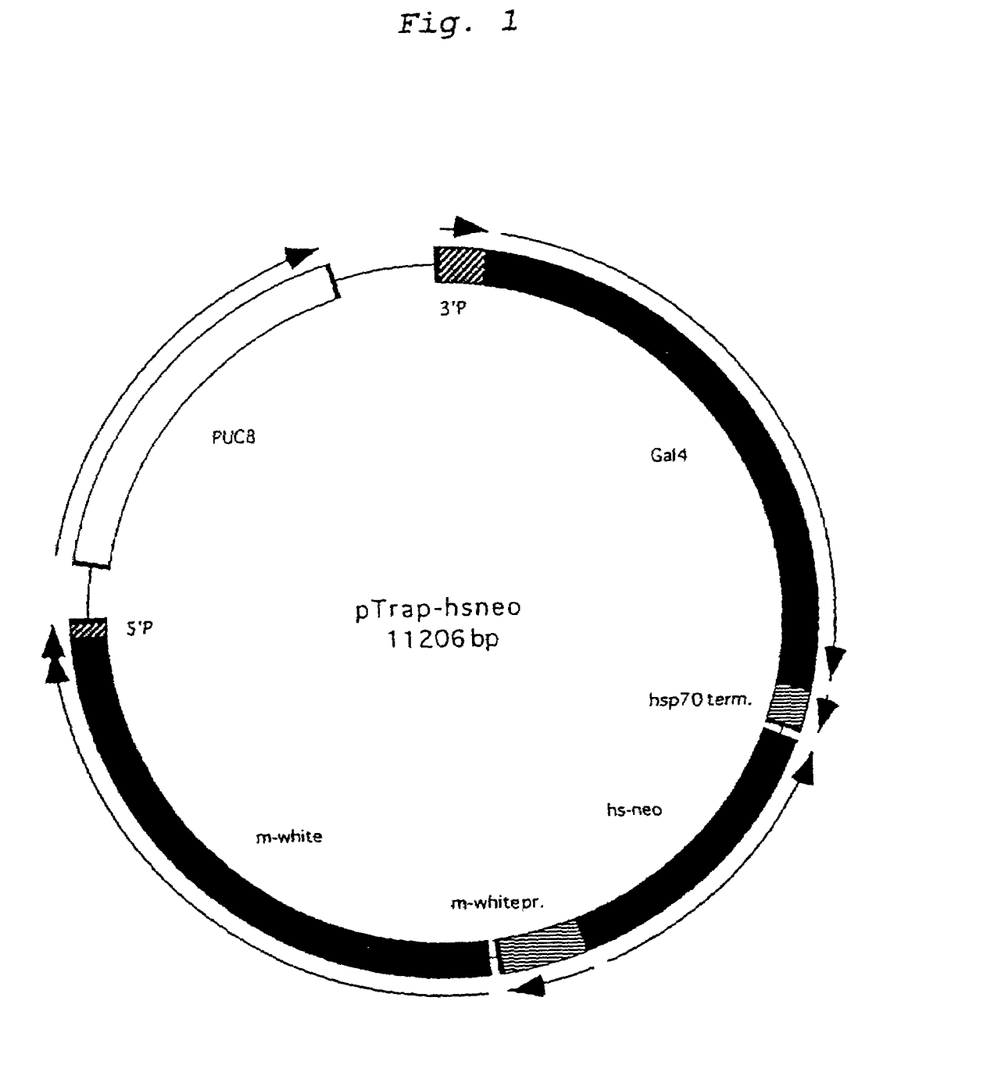
FIG. 1 shows the schematic map of the vector of this invention, pTrap-hsneo.

FIG. 1 shows the schematic map of the gene trap construct (pTrap-hsneo), and SEQ ID No.1 is the complete nucleotide sequence of the vector pTrap-hsneo.

Another gene trap construct, pTrap-G4-p53 (FIG. 2) is created by replacing the Gal4 coding sequence of plasmid pTrap-hsneo with a Gal4 DNA binding domain-P53 fusion gene (Clontech, Matchmaker Two Hybrid System, #K1605-1). When this construct coexists in the genome of the same fly with another vector, pCasperhs-G4-LT (FIG. 3) containing a heatshock promoter directed Gal4 activator domain-large T antigen (Clontech, Matchmaker Two Hybrid System, #K1605-1) fusion gene, the assembly of a functional Gal4 molecule, through p53-large T antigen interaction, can be regulated by external heatshock.

Figure 2:
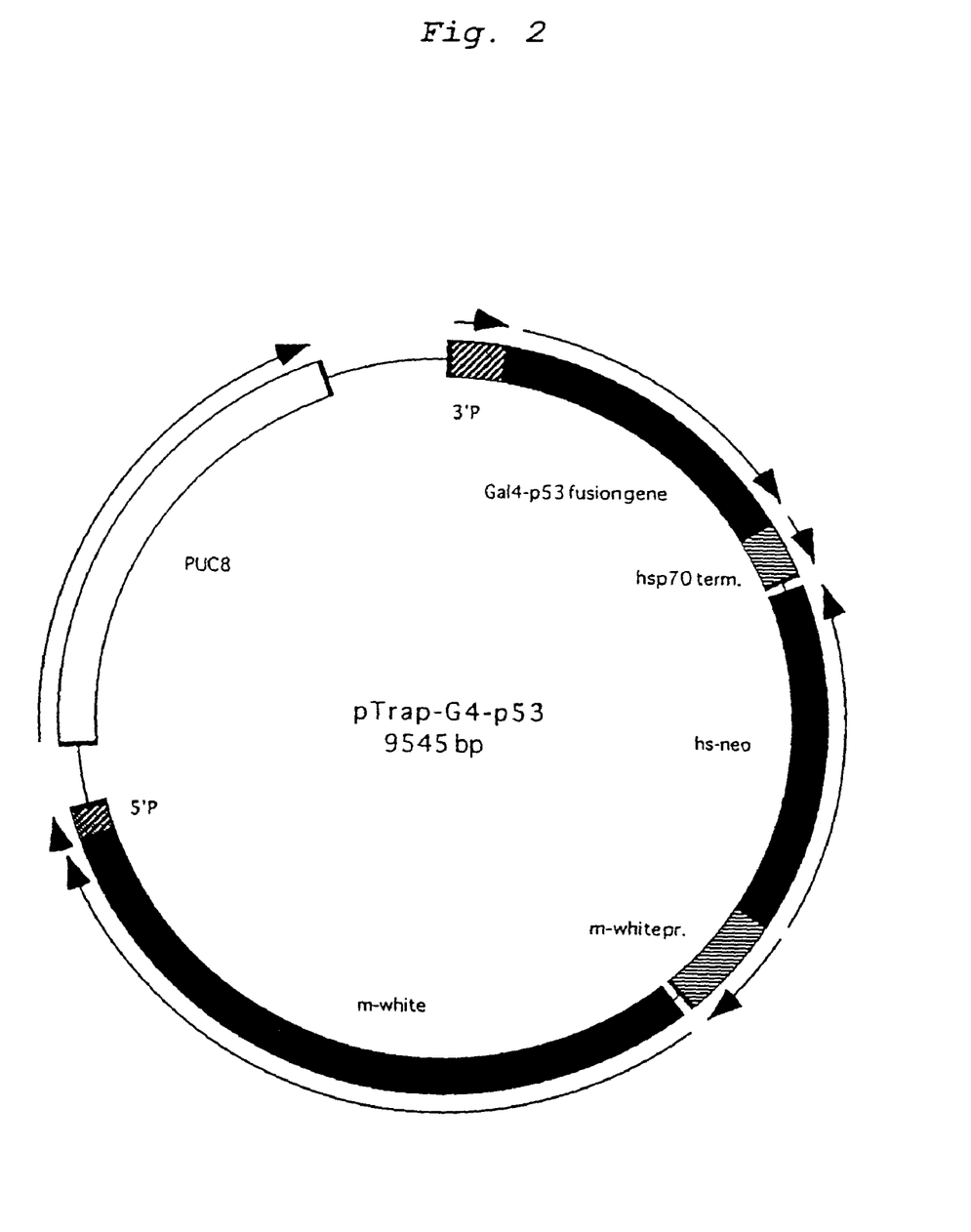
FIG. 2 shows the schematic map of the vector of this invention, pTrap-G4-p53.
Figure 3:
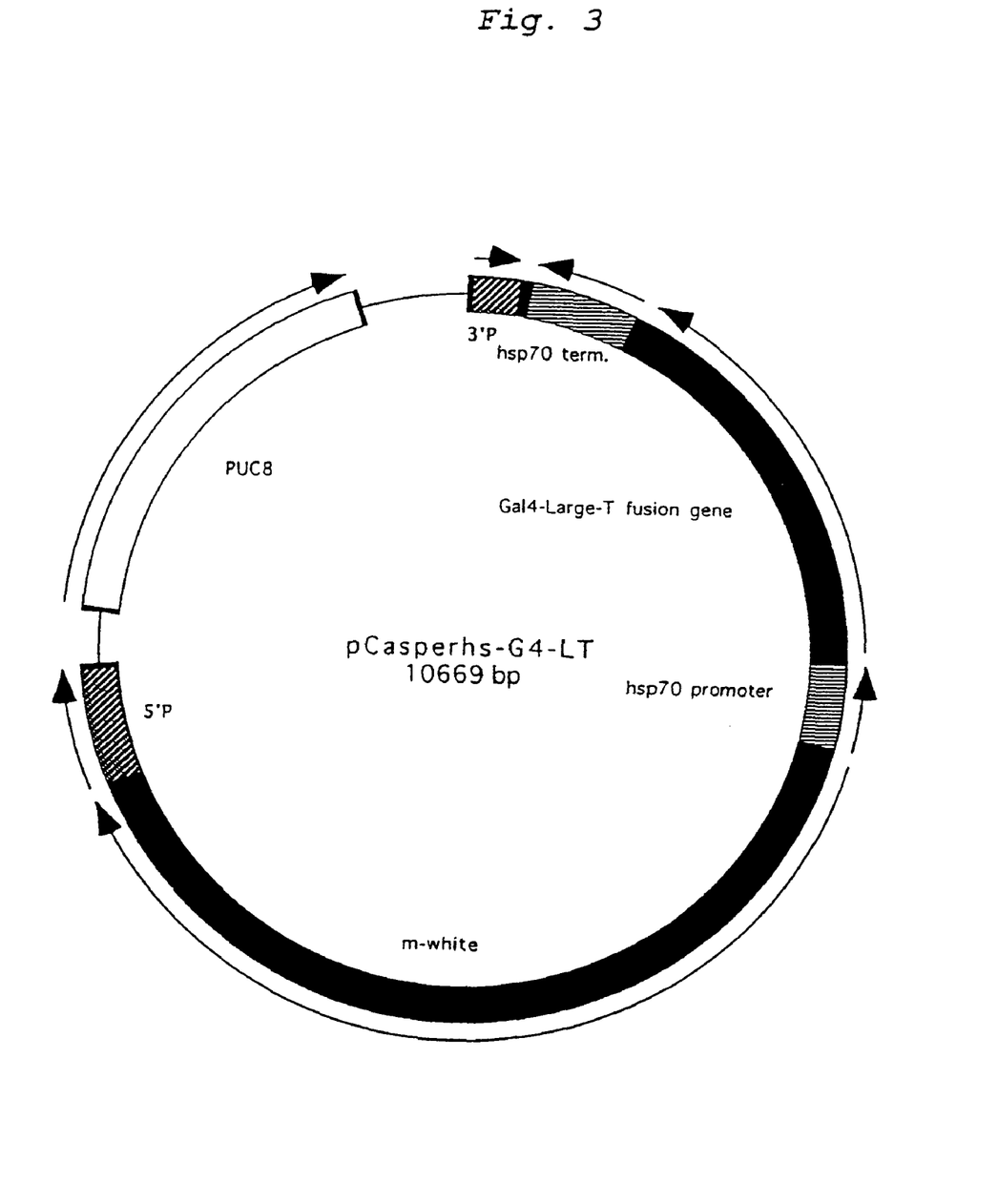
FIG. 3 shows the schematic map of the vector of this invention, pCasperhs-G4-LT.

In this way, the possibility of an intentional temporary control of Gal4 activity becomes available. In other words, the Gal4 expression in a pattern as already determined spatially by the promoter of the trapped gene now can be induced at any desired stage of development by external heatshock.

Figure 4:
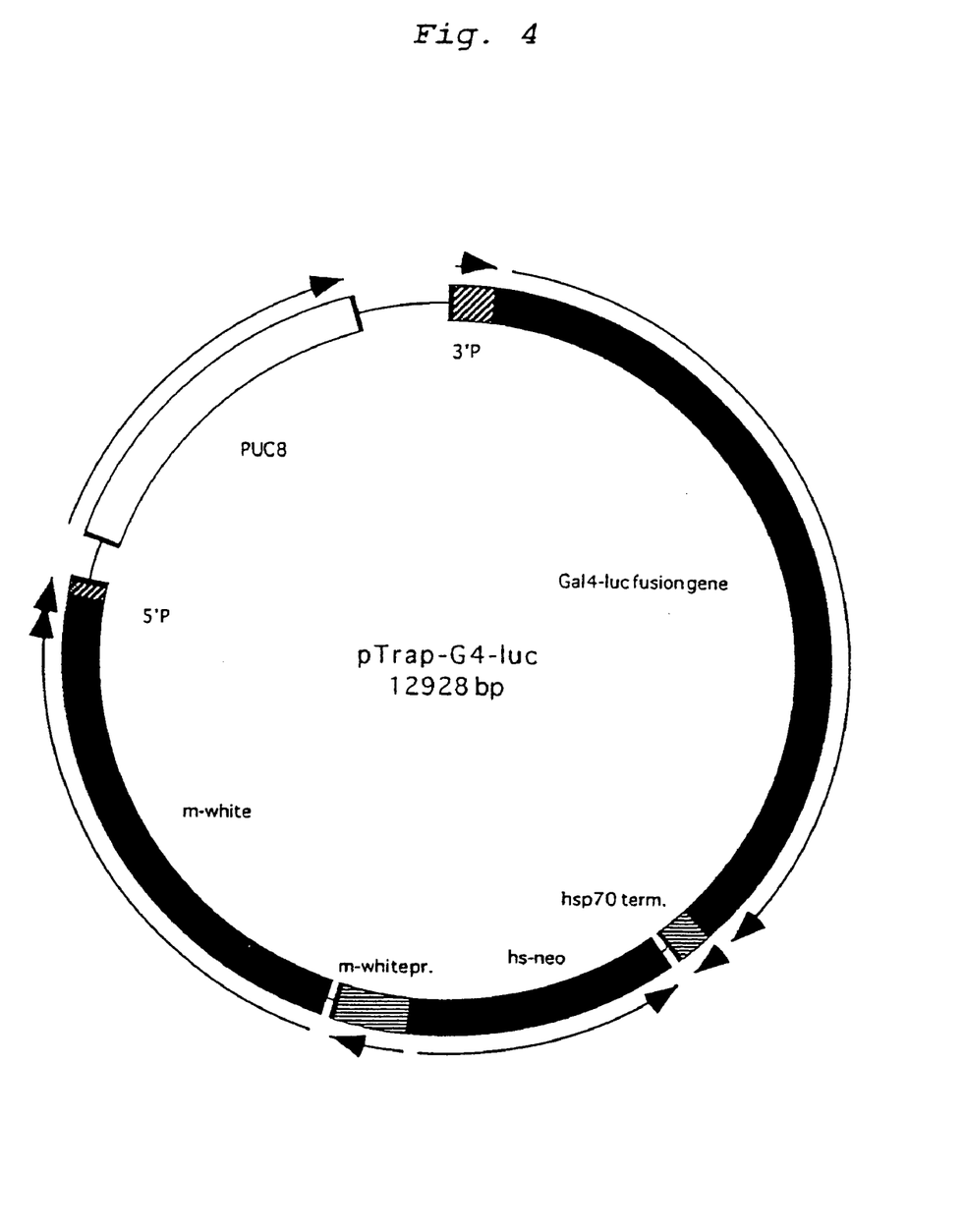
FIG. 4 shows the schematic map of the vector of this invention, pTrap-G4-luc.

In order to make the detection of Gal4 expression easier, the Gal4 gene in another construct is replaced with a Gal4-firefly luciferase fusion gene to get pTrap-G4-luc (FIG. 4). This artificial gene is ceding for a fusion polypeptide which has preserved both enzymatic activities.

The easy measuring of luciferase activity by luminoassay (Brandes et al., Neuron, 16:687–694, 1996) makes the detection of Gal4 activity comfortable in every single living fly.

Then, one of the best mode of the second or third invention, a method for gene trapping using the vector system, is described in detail.

(1) Screening:

The gene trap vector constructs can be introduced into the genome of a white minus fly by microinjection. The selection of primary transformants is possible by using G418, an analog of neomycin, resistance conferred by hs-neo gene. (When performing transformation experiments with these constructs it's turned out that the truncated mini-white gene generally provides a very slight yellow eye color which could be distinguished from w-minus phenotype in most of the cases, therefore G418 selection apparently is not necessary.)

After a line with the gene trap construct is being established, the secondary transformants can be generated on the usual way by crossing the original line with a so-called jumpstarter containing the transposase expressing delta 2–3 genetic element.

Usually a certain percentage, between 4 and 8, of the secondary transformants have much stronger eye color (deep orange or reddish) than the ancestor fly indicating that the construct was being inserted downstream of a promoter and now the mini-white gene is using the transcriptional "facilities" of that gene (e.g.: poly-adenylation site and transcriptional terminator) instead of its removed ones. They are the most likely candidates for successful gene trap events. In case of these lines the vector probably has been inserted either into an intron of a gene or upstream from the first intron into the 5' UTR in proper orientation (that is the direction of transcription is same for the "trapped gene" and the mini-white (and Gal4) genes as well). The mini-white gene has its own promoter therefore its expression pattern is supposed to be largely independent from that of the trapped gene.

These positive lines are to be checked in the next step for Gal4 expression by crossing them with a "marker" line harboring a UAS-luciferase reporter gene construct. (When using pTrap-G4-luc vector, this step is obviously not necessary.) Usually very strong correlation was found between eye color and Gal4 expression: more than 90% of the lines having strong eye color proved to be expressing Gal4 by means of luciferase assay using luminometer (Brandes et al., Neuron, 16:687–692, 1996).

Figure 5:
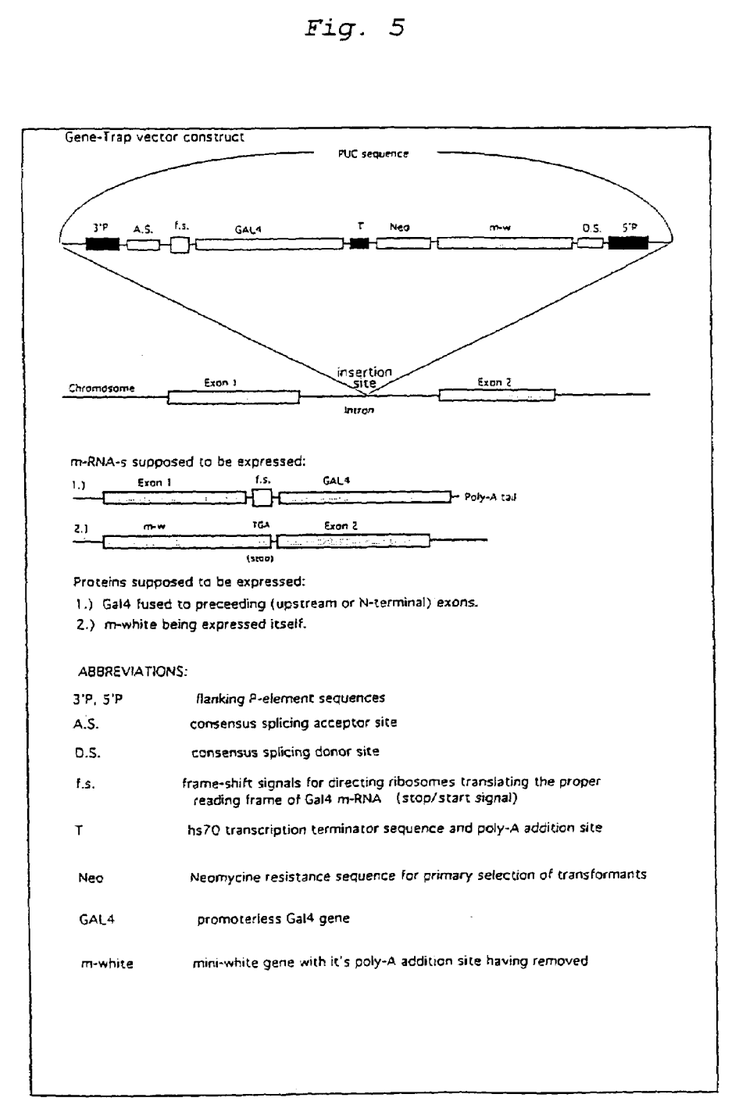
FIG. 5 shows the schematic drawing of a fly genome to which the vector of this invention is inserted for cloning.

(2) Cloning:

When the gene trap construct is being inserted into an intron of an endogenous gene, the marker genes of the construct are supposed to be spliced at mRNA level to the exons of the trapped gene by using the artificial splicing acceptor and donor sites. More exactly while the Gal4 mRNA should be joined to the exon(s) located upstream of the insertion site, at the same time the mini-white mRNA is fused to the following exon(s) accomplishing the dual tagging of the trapped gene (FIG. 5).

This feature can be used for quickly and easily identifying the trapped gene by means of 3' and 5' RACE (Rapid Amplification of cDNA Ends) experiments. Even cloning and sequencing only a part of the caught mRNA still provides reasonable chance to find homologous mRNAs in the BDGP (Berkeley *Drosophila* Genome Project) EST (Expressed Sequence Tag) library.

With these approaches, the identification of an already cloned gene can take less then a week compared to the usually more than one year period in average when analyzing a mutant created by some enhancer trap construct.

It's well-known from the literature and the present inventors also have experienced that P-element vectors tend to integrate into or near the 5' UTR of active genes. (The present inventors found that in these cases if the insertion occurred upstream from the first intron, and therefore the artificial splicing acceptor site could not be utilized, the Gal4 gene was expressed by read-through transcription from the nearby promoter.)

The advantage of this tendency can be taken by cloning and sequencing the flanking genomic sequences of the insertion site by inverse or vectorette PCR or by plasmid rescue using suitable restriction digestion to recover the neomycin resistance gene of the construct. Then again the BDGP library can be searched to find any significant matching.

(3) Rescue:

The only reliable way to confirm that any observed mutant phenotype is really the consequence of the P-element insertion is to rescue that particular phenotype. Expectedly the phenotype (some alteration from wild type fly)is caused by changed expression of gene(s) disturbed by insertion of the P-element. The rescue can be made by expressing the cDNA of the suspected gene most preferable with identical spatial and temporary pattern than that of the gene itself.

As it was expected, the vector constructs of the first invention usually cause strong phenotypes. It's not surprising at all because the trapped genes are supposed to be split into two parts on mRNA level resulting in null mutants in majority of the cases. Accordingly mutants obtained by this method frequently show homozygous lethality or sterility. Hypomorphic mutants can be obtained by forcing imprecise excision of the gene trap P-element construct.

As mentioned above, the Gal4 expression is obliged to reflect precisely to that of the trapped gene simply because the Gal4 gene has not its own promoter and they share a common, fused mRNA.

This identical expression provides unique opportunity to rescue the mutant phenotype by crossing this fly with another one harboring the UAS directed, cloned cDNA of the trapped gene.

In this way either the original, homozygous null mutant gene trap fly or any transheterozygous derivative of that with some hypomorphic allele over the null mutant allele can be rescued.

(4) Determination of Spatial and Developmental Expression Pattern of the Trapped Gene:

Histochemical determination of the spatially and temporarily controlled expression of any trapped gene is also easy following introduction of a UAS-lacZ construct into the genome of the same fly and performing either X-gal or antibody staining for beta-galactosidase.

(5) Mosaic Analysis:

Possession of a large collection of fly lines with different, characteristic and, in the case of the pTrap-G4-p53/ pCasperhs-G4-TL vector system, inducible Gal4 expression pattern makes feasible carrying out mosaic analysis of virtually any gene of interest by directing the expression of their UAS-constructs on a mutant background with different Gal4 expression patterns.

This approach can answer the question of where and when that particular gene is required to be expressed to rescue the mutant phenotype.

Similarly, any gene can be expressed in different ectopic patterns to generate new dominant mutant phenotypes. This approach might help to conclude the role of that particular gene and to identify the pathway, in which it's involved

EXAMPLE

The following example illustrates a specific embodiment of the various aspects of the invention. This example is not intended to limit the invention in any manner.

Figure 6:
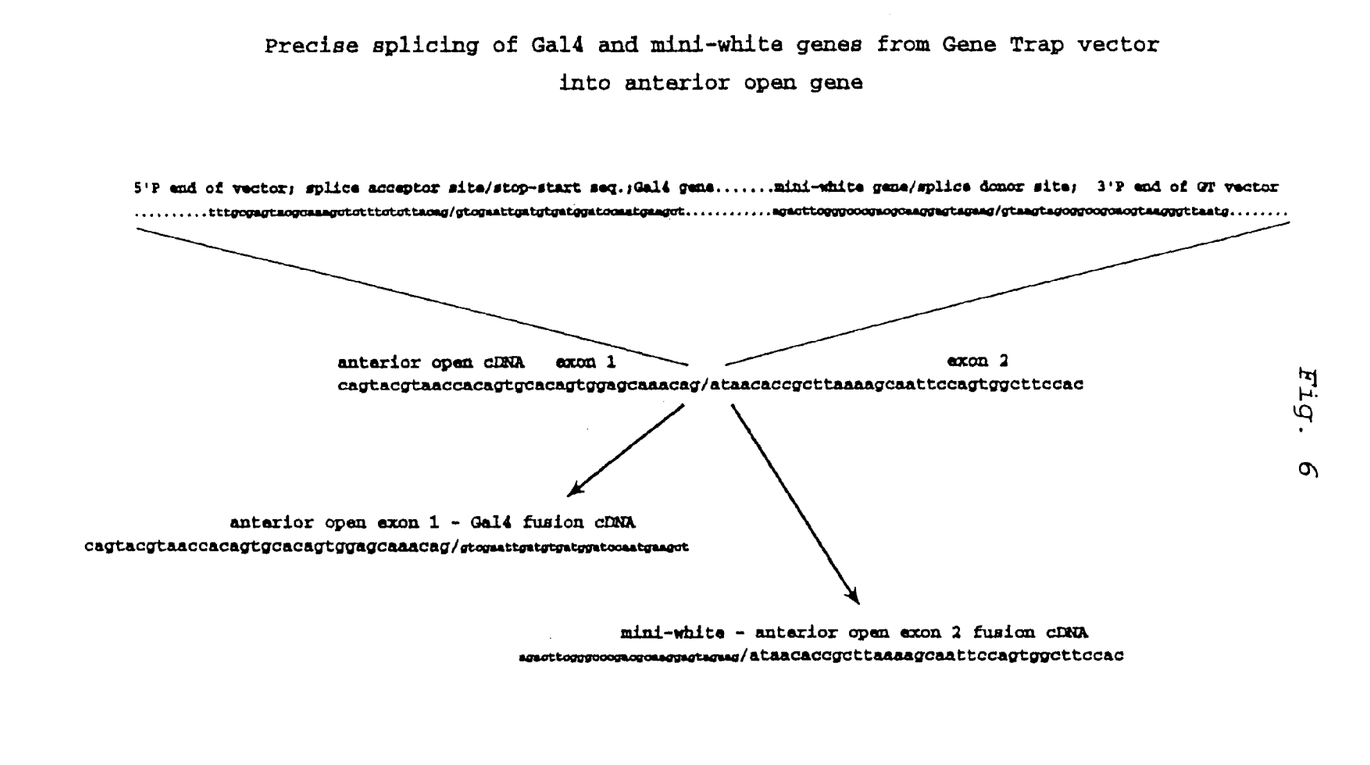
FIG. 6 shows the results of sequencing RT-PCR products of aop-Gal4 and m-white-aop fusion mRNAs.

FIG. 6 shows the results of sequencing RT-PCR products of aop-Gal4 and m-white-aop fusion mRNAs.

The template was total RNA prepared from a positive gene trap line which has the vector pTrap-hsneo being integrated into the first intron of the well-known aop (anterior open/pokkuri/yan) developmental gene. The sequences confirm that both splicing occurred precisely at that particular nucleotides of the artificial regulatory sequences where it was expected.

Figure 7:
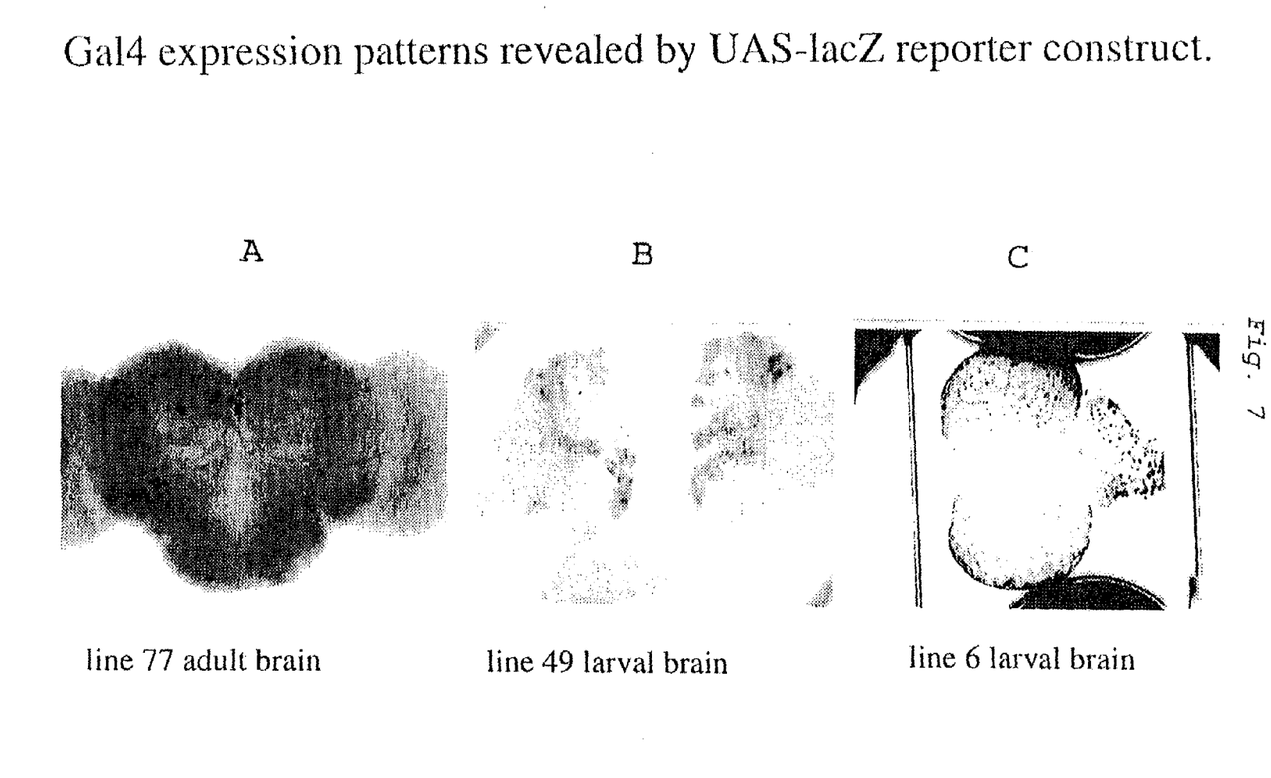
FIG. 7 presents pictures of characteristic beta-galactosidase staining patterns in different parts of the fly brain resulted from crossing positive gene trap lines with flies harboring a UAS-lacZ construct.

On FIG. 7, there are pictures of characteristic beta-galactosidase staining patterns in different parts of the fly brain resulted from crossing positive gene trap lines with flies harboring a UAS-lacZ construct.

The vector system of this invention offers an exceptional opportunity for easy and fast cloning of the gene responsible for the observed phenotype. Furthermore, by using the UAS-driven coding sequence of any gene of interest, that particular gene can be expressed in identical patterns than those of the trapped genes and these expressions can be regulated temporarily at any desired developmental stage.

What is claimed is:

1. A vector for trapping an unknown gene of *Drosophila melanogaster*, which is a recombinant plasmid comprising a recombinant P-element, wherein the P-element comprises the following nucleotide sequences in this order:
   an artificial consensus splicing acceptor site;
   a synthetic stop/start sequence;
   a promoterless reporter gene;
   a heatshock promoter directed neomycin phosphotransferase gene; and
   a mini-white gene under control of a white gene promoter and comprising a synthetic splicing donor site in place of a poly-A addition site.

2. The vector of claim 1, wherein the recombinant plasmid is based on pCasper3.

3. The vector of claim 1, wherein the promoterless reporter gene is a Gal4 gene.

4. A vector for trapping an unknown gene of *Drosophila melanogaster*, which vector has the nucleotide sequence of SEQ ID No. 1.

5. The vector of claim 1, wherein the promoterless reporter gene is a Gal4 DNA binding domain-P53 fusion gene.

6. The vector of claim 1, wherein the promoterless reporter gene is a Gal4-firefly luciferase fusion gene.

7. A vector made by inserting a heatshock promoter directed Gal4 activator domain-large T antigen fusion gene into the polycloning site of pCasperhs.

8. A method for trapping an unknown gene of *Drosophila melanogaster* by using a vector which is a recombinant plasmid comprising a recombinant P-element, wherein the P-element comprises the following nucleotide sequences in this order:
   an artificial consensus splicing acceptor site;
   a synthetic stop/start sequence;
   a promoterless Gal4 reporter gene;
   a heatshock promoter directed neomycin phosphotransferase gene; and
   a mini-white gene under control of a white gene promoter and comprising a synthetic splicing donor site in place of a poly-A addition site, which method comprises the steps of:
   (a) introducing the vector into the genome of a white minus fly;
   (b) selecting primary transformants containing the vector;
   (c) crossing the primary transformants with a transposase source fly strain to force the P-element to jump into other locations;
   (d) selecting secondary transformants by selecting flies produced from the cross of step (c) having strong eye color,
   (e) crossing the secondary transformants with a Gal4-UAS (Upstream Activator Sequence)-luciferase harboring fly strain and measuring expression of the promoterless Gal4 reporter gene in the secondary transformants; and
   (f) identifying the trapped gene by cloning and sequencing cDNA comprising the Gal4 gene and cDNA comprising the mini-white gene.

9. The method according to claim 8, wherein the recombinant plasmid is based on pCasper3.

10. The method according to claim 8, wherein in step (b) primary transformants resistant to G418 are selected.

11. A method for trapping an unknown gene of *Drosophila melanogaster* by using a vector A and a vector B;
   wherein vector A is a recombinant plasmid comprising a recombinant P-element, wherein the P-element comprises the following nucleotide sequences in this order:
   an artificial consensus splicing acceptor site;
   a synthetic stop/start sequence;
   a promoterless Gal4 DNA binding domain-P53 fusion gene as a reporter gene;
   a heatshock promoter directed neomycin phosphotransferase gene; and
   a mini-white gene under control of a white gene promoter and comprising a synthetic splicing donor site in place of a poly-A addition site, and vector B is derived from pCasperhs by inserting a heat-shock promoter directed Gal4 activator domain-large T antigen fusion gene within the polycloning site of pCasperhs, which method comprises the steps of:
(a) introducing each of the vectors A and B into the genomes of separate white minus flies;
(b) selecting primary transformants for the vector A which are resistant to G418 and selecting primary transformants for the vector B which have an eye color other than white;
(c) crossing the primary transformants for the vector A with a transposase source fly strain to force the P-element to jump into other locations;
(d) selecting secondary transformants for the vector A by selecting flies produced by the cross of step (c) that have strong eye color;
(e) crossing the secondary transformants with the primary transformants for the vector B to obtain flies harboring the P-element and vector B;
(f) crossing the flies obtained in the step (e) with a Gal4-UAS-luciferase harboring fly strain and measuring luciferase expression of the resultant flies after a heatshock treatment; and
(g) identifying the trapped gene by cloning and sequencing cDNA comprising the reporter gene and cDNA comprising the mini-white gene.

12. The method according to claim 11, wherein the vector A is based on pCasper3.

13. A method for trapping an unknown gene of *Drosophila melanogaster* by using a vector which is a recombinant plasmid comprising a recombinant P-element, wherein the P-element comprises the following nucleotide sequences in this order:
an artificial consensus splicing acceptor site;
a synthetic stop/start sequence;
a promoterless Gal4-firefly luciferase fusion gene as a reporter gene;
a heatshock promoter directed neomycin phosphotransferase gene; and
a mini-white gene under control of a white gene promoter and comprising a synthetic splicing donor site in place of a poly-A addition site, which method comprises the steps of:
(a) introducing the vector into the genome of a white minus fly;
(b) selecting primary transformants containing the vector;
(c) crossing the primary transformants with a transposase source fly strain to force the P-element to jump into other locations;
(d) selecting secondary transformants by selecting flies produced from the cross of step (c) having strong eye color;
(e) measuring expression of Gal4-firefly luciferase fusion gene in the secondary transformants without crossing the secondary transformants with a Gal4-UAS-luciferase harboring strain; and
(f) identifying the trapped gene by cloning and sequencing cDNA comprising the reporter gene and cDNA comprising the mini-white gene.

* * * * *

SEQUENCE LISTING

<160> NUMBER OF SEQ ID NOS: 7

<210> SEQ ID NO 1
<211> LENGTH: 11206
<212> TYPE: DNA
<213> ORGANISM: Artificial sequence
<220> FEATURE:
<221> NAME/KEY: 3'P sequence
<222> LOCATION: (1)..(237)
<220> FEATURE:
<221> NAME/KEY: synthetic splicing acceptor site and stop/start sequence
<222> LOCATION: (238)..(274)
<220> FEATURE:
<221> NAME/KEY: Gal4 gene (coding region and 3'UTR)
<222> LOCATION: (275)..(3164)
<220> FEATURE:
<221> NAME/KEY: hsp70 terminator
<222> LOCATION: (3165)..(3426)
<220> FEATURE:
<221> NAME/KEY: synthetic junction sequence
<222> LOCATION: 3427-3457
<220> FEATURE:
<221> NAME/KEY: heat shock promoter directed neomycine resistance gene
      on complementer strand
<222> LOCATION: (3458)..(4907)
<220> FEATURE:
<221> NAME/KEY: mini-white gene
<222> LOCATION: (4908)..(8275)
<220> FEATURE:
<221> NAME/KEY: synthetic splicing donor site
<222> LOCATION: (8276)..(8299)
<220> FEATURE:
<221> NAME/KEY: 5'P sequence
<222> LOCATION: (8300)..(8446)
<220> FEATURE:
<221> NAME/KEY: bacterial part of pCasper3 shuttle vector including
      complete pUC8 sequence
<222> LOCATION: (8447)..(11206)
<220> FEATURE:
<221> NAME/KEY: synthetic DNA
<222> LOCATION: (238)..(274)
      (3427)..(3457)
      (4908)..(4914)(8276)..(8299)
<223> OTHER INFORMATION: Description of Artificial Sequence: Synthetic
      DNA

<400> SEQUENCE: 1
catgatgaaa taacataagg tggtcccgtc ggcaagagac atccacttaa cgtatgcttg      60
caataagtgc gagtgaaagg aatagtattc tgagtgtcgt attgagtctg agtgagacag     120
cgatatgatt gttgattaac ccttagcatg tccgtggggt ttgaattaac tcataatatt     180
aattagacga aattatttt aaagttttat ttttaataat ttgcgagtac gcaaagctct     240
ttctcttaca ggtcgaattg atgtgatgga tccaatgaag ctactgtctt ctatcgaaca     300
agcatgcgat atttgccgac ttaaaaagct caagtgctcc aaagaaaaac cgaagtgcgc     360
caagtgtctg aagaacaact gggagtgtcg ctactctccc aaaaccaaaa ggtctccgct     420
gactagggca catctgacag aagtggaatc aaggctagaa agactggaac agctatttct     480
actgattttt cctcgagaag accttgacat gattttgaaa atggattctt tacaggatat     540
aaaagcattg ttaacaggat tatttgtaca agataatgtg aataaagatg ccgtcacaga     600
tagattggct tcagtggaga ctgatatgcc tctaacattg agacagcata gaataagtgc     660
gacatcatca tcggaagaga gtagtaacaa aggtcaaaga cagttgactg tatcgattga     720
ctcggcagct catcatgata actccacaat tccgttggat tttatgccca gggatgctct     780
tcatggattt gattggtctg aagaggatga catgtcggat ggcttgccct tcctgaaaac     840

-continued

```
ggaccccaac aataatgggt tctttggcga cggttctctc ttatgtattc ttcgatctat      900
tggctttaaa ccggaaaatt acacgaactc taacgttaac aggctcccga ccatgattac      960
ggatagatac acgttggctt ctagatccac aacatcccgt ttacttcaaa gttatctcaa     1020
taattttcac ccctactgcc ctatcgtgca ctcaccgacg ctaatgatgt tgtataataa     1080
ccagattgaa atcgcgtcga aggatcaatg gcaaatcctt tttaactgca tattagccat     1140
tggagcctgg tgtatagagg gggaatctac tgatatagat gttttttact atcaaaatgc     1200
taaatctcat ttgacgagca aggtcttcga gtcaggttcc ataattttgg tgacagccct     1260
acatcttctg tcgcgatata cacagtggag gcagaaaaca atactagct ataattttca      1320
cagcttttcc ataagaatgg ccatatcatt gggcttgaat agggacctcc cctcgtcctt     1380
cagtgatagc agcattctgg aacaaagacg ccgaatttgg tggtctgtct actcttggga     1440
gatccaattg tccctgcttt atggtcgatc catccagctt tctcagaata caatctcctt     1500
cccttcttct gtcgacgatg tgcagcgtac cacaacaggt cccaccatat atcatggcat     1560
cattgaaaca gcaaggctct tacaagtttt cacaaaaatc tatgaactag acaaaacagt     1620
aactgcagaa aaagtcccta tatgtgcaaa aaatgcttg atgatttgta atgagattga      1680
ggaggtttcg agacaggcac caaagttttt acaaatggat atttccacca ccgctctaac     1740
caatttgttg aaggaacacc cttggctatc ctttacaaga ttcgaactga agtggaaaca     1800
gttgtctctt atcatttatg tattaagaga ttttttcact aattttaccc agaaaaagtc     1860
acaactagaa caggatcaaa atgatcatca aagttatgaa gttaaacgat gctccatcat     1920
gttaagcgat gcagcacaaa gaactgttat gtctgtaagt agctatatgg acaatcataa     1980
tgtcacccca tattttgcct ggaattgttc ttattacttg ttcaatgcag tcctagtacc     2040
cataaagact ctactctcaa actcaaaatc gaatgctgag aataacgaga ccgcacaatt     2100
attacaacaa attaacactg ttctgatgct attaaaaaaa ctggccactt ttaaaatcca     2160
gacttgtgaa aaatacattc aagtactgga agaggtatgt gcgccgtttc tgttatcaca     2220
gtgtgcaatc ccattaccgc atatcagtta taacaatagt aatggtagcg ccattaaaaa     2280
tattgtcggt tctgcaacta tcgcccaata ccctactctt ccggaggaaa atgtcaacaa     2340
tatcagtgtt aaatatgttt ctcctggctc agtagggcct tcacctgtgc cattgaaatc     2400
aggagcaagt ttcagtgatc tagtcaagct gttatctaac cgtccaccct ctcgtaactc     2460
tccagtgaca ataccaagaa gcacaccttc gcatcgctca gtcacgcctt ttctagggca     2520
acagcaacag ctgcaatcat tagtgccact gaccccgtct gctttgtttg gtggcgccaa     2580
ttttaatcaa agtgggaata ttgctgatag ctcattgtcc ttcactttca ctaacagtag     2640
caacggtccg aacctcataa caactcaaac aaattctcaa gcgctttcac aaccaattgc     2700
ctcctctaac gttcatgata acttcatgaa taatgaaatc acggctagta aaattgatga     2760
tggtaataat tcaaaaccac tgtcacctgg ttggacggac caaactgcgt ataacgcgtt     2820
tggaatcact acagggatgt ttaataccac tacaatggat gatgtatata actatctatt     2880
cgatgatgaa gataccccac caaacccaaa aaaagagtaa aatgaatcgt agatactgaa     2940
aaaccccgca agttcacttc aactgtgcat cgtgcaccat ctcaatttct ttcatttata     3000
catcgttttg ccttctttta tgtaactata ctcctctaag tttcaatctt ggccatgtaa     3060
cctctgatct atagaatttt ttaaatgact agaattaatg cccatctttt ttttggacct     3120
aaattcttca tgaaaatata ttacgagggc ttattcagaa gcttatcgat accgtcgact     3180
aaagccaaat agaaattatt cagttctggc ttaagttttt aaaagtgata ttatttattt     3240
```

-continued

```
ggttgtaacc aaccaaaaga atgtaaataa ctaatacata attatgttag ttttaagtta    3300
gcaacaaatt gattttagct atattagcta cttggttaat aaatagaata tatttattta    3360
aagataattc gtttttattg tcagggagtg agtttgctta aaaactcgtt tagatccact    3420
agaaggaccg cggctcctcg accggatcga aggagggcg  aagaactcca gcatgagatc    3480
cccgcgctgg aggatcatcc agccggcgtc cggaaaacg  attccgaagc ccaacctttc    3540
atagaaggcg gcggtggaat cgaaatctcg tgatggcagg ttgggcgtcg cttggtcggt    3600
catttcgaac cccagagtcc cgctcagaag aactcgtcaa gaaggcgata gaaggcgatg    3660
cgctgcgaat cgggagcggc gataccgtaa agcacgagga agcggtcagc ccattcgccg    3720
ccaagctctt cagcaatatc acgggtagcc aacgctatgt cctgatagcg gtccgccaca    3780
cccagccggc cacagtcgat gaatccagaa aagcggccat tttccaccat gatattcggc    3840
aagcaggcat cgccatgggt cacgacgaga tcctcgccgt cgggcatgcg cgccttgagc    3900
ctggcgaaca gttcggctgg cgcgagcccc tgatgctctt cgtccagatc atcctgatcg    3960
acaagaccgg cttccatccg agtacgtgct cgctcgatgc gatgtttcgc ttggtggtcg    4020
aatgggcagg tagccggatc aagcgtatgc agccgccgca ttgcatcagc catgatggat    4080
actttctcgg caggagcaag gtgagatgac aggagatcct gccccggcac ttcgcccaat    4140
agcagccagt cccttcccgc ttcagtgaca acgtcgagca cagctgcgca aggaacgccc    4200
gtcgtggcca gccacgatag ccgcgctgcc tcgtcctgca gttcattcag ggcaccggac    4260
aggtcggtct tgacaaaaag aaccgggcgc ccctgcgctg acagccggaa cacggcggca    4320
tcagagcagc cgattgtctg ttgtgcccag tcatagccga atagcctctc cacccaagcg    4380
gccggagaac ctgcgtgcaa tccatcttgt tcaatcatgc gaaacgatcc tcatcctgtc    4440
tcttgatcag atcccctatt cagagttctc ttcttgtatt caataattac ttcttggcag    4500
atttcagtag ttgcagttga tttacttggt tgctggttac ttttaattga ttcacttttaa   4560
cttgcacttt actgcagatt gtttagcttg ttcagctgcg cttgtttatt tgcttagctt    4620
tcgcttagcg acgtgttcac tttgcttgtt tgaattgaat tgtcgctccg tagacgaagc    4680
gcctctattt atactccggc gctctttttcg cgaacattcg aggcgcgctc tctcgaacca    4740
acgagagcag tatgccgttt actgtgtgac agagtgagag agcattagtg cagagaggga    4800
gagacccaaa aagaaaagag agaataacga ataacggcca gagaaatttc tcgagttttc    4860
tttctgccaa acaaatgacc taccacaata accagtttgt tttgggatct agtccctaat    4920
tctagtatgt atgtaagtta ataaaaccct ttttgggaga atgtagattt aaaaaaacat    4980
atttttttt  tattttttac tgcactggac atcattgaac ttatctgatc agttttaaat    5040
ttacttcgat ccaagggtat ttgaagtacc aggttctttc gattacctct cactcaaaat    5100
gacattccac tcaaagtcag cgctgtttgc ctccttctct gtccacagaa atatcgccgt    5160
ctctttcgcc gctgcgtccg ctatctcttt cgccaccgtt tgtagcgtta cctagcgtca    5220
atgtccgcct tcagttgcac tttgtcagcg gtttcgtgac gaagctccaa gcggtttacg    5280
ccatcaatta aacacaaagt gctgtgccaa aactcctctc gcttcttatt tttgtttgtt    5340
ttttgagtga ttggggtggt gattggtttt gggtgggtaa gcaggggaaa gtgtgaaaaa    5400
tcccggcaat gggccaagag gatcaggagc tattaattcg cggaggcagc aaacacccat    5460
ctgccgagca tctgaacaat gtgagtagta catgtgcata catcttaagt tcacttgatc    5520
tataggaact gcgattgcaa catcaaattg tctgcggcgt gagaactgcg acccacaaaa    5580
```

-continued

```
atcccaaacc gcaatcgcac aaacaaatag tgacacgaaa cagattattc tggtagctgt    5640
gctcgctata taagacaatt tttaagatca tatcatgatc aagacatcta aaggcattca    5700
ttttcgacta cattcttttt tacaaaaaat ataacaacca gatattttaa gctgatccta    5760
gatgcacaaa aataaaataa agtataaaac ctacttcgta ggatacttcg ttttgttcgg    5820
ggttagatga gcataacgct tgtagttgat atttgagatc ccctatcatt gcagggtgac    5880
agcggacgct tcgcagagct gcattaacca gggcttcggg caggcaaaaa actacggcac    5940
gctcctgcca cccagtccgc cggaggactc cggttcaggg agcggccaac tagccgagaa    6000
cctcacctat gcctggcaca atatggacat cttggggcg gtcaatcagc cgggctccgg    6060
atggcggcag ctggtcaacc ggacacgcgg actattctgc aacgagcgac ataccggc      6120 gcccaggaaa catttgctca agaacggtga gtttctattc gcagtcggct gatctgtgtg    6180
aaatcttaat aaagggtcca attaccaatt tgaaactcag tttgcggcgt ggcctatccg    6240
ggcgaacttt tggccgtgat gggcagttcc ggtgccggaa agacgaccct gctgaatgcc    6300
cttgcctttc gatcgccgca gggcatccaa gtatcgccat ccgggatgcg actgctcaat    6360
ggccaacctg tggacgccaa ggagatgcag gccaggtgcg cctatgtcca gcaggatgac    6420
ctctttatcg gctccctaac ggccagggaa cacctgattt tccaggccat ggtgcggatg    6480
ccacgacatc tgacctatcg gcagcgagtg gcccgcgtgg atcaggtgat ccaggagctt    6540
tcgctcagca aatgtcagca cacgatcatc ggtgtgcccg gcagggtgaa aggtctgtcc    6600
ggcggagaaa ggaagcgtct ggcattcgcc tccgaggcac taaccgatcc gccgcttctg    6660
atctgcgatg agcccaccctc cggactggac tcatttaccg cccacagcgt cgtccaggtg    6720
ctgaagaagc tgtcgcagaa gggcaagacc gtcatcctga ccattcatca gccgtcttcc    6780
gagctgtttg agctctttga caagatcctt ctgatggccg agggcagggt agctttcttg    6840
ggcactccca gcgaagccgt cgacttcttt tcctagtgag ttcgatgtgt ttattaaggg    6900
tatctagcat tacattacat ctcaactcct atccagcgtg ggtgcccagt gtcctaccaa    6960
ctacaatccg gcggactttt acgtacaggt gttggccgtt gtgccggac gggagatcga    7020 gtcccgtgat cggatcgcca agatatgcga caattttgct attagcaaag tagcccggga    7080
tatggagcag ttgttggcca ccaaaaattt ggagaagcca ctggagcagc ggagaatgg    7140 gtacacctac aaggccacct ggttcatgca gttccgggcg gtcctgtggc gatcctggct    7200
gtcggtgctc aaggaaccac tcctcgtaaa agtgcgactt attcagacaa cggtgagtgg    7260
ttccagtgga aacaaatgat ataacgctta caattcttgg aaacaaattc gctagatttt    7320
agttagaatt gcctgattcc acaccttct tagttttttt caatgagatg tatagtttat    7380
agttttgcag aaaataaata aatttcattt aactcgcgaa catgttgaag atatgaatat    7440
taatgagatg cgagtaacat ttaatttgc agatggttgc catcttgatt ggcctcatct    7500
ttttgggcca acaactcacg caagtgggcg tgatgaatat caacgagcc atcttcctct    7560 tcctgaccaa catgaccttt caaaacgtct ttgccacgat aaatgtaagt cttgtttaga    7620
atacatttgc atattaataa tttactaact ttctaatgaa tcgattcgat ttaggtgttc    7680
acctcagagc tgccagtttt tatgagggag gcccgaagtc gactttatcg ctgtgacaca    7740
tactttctgg gcaaaacgat tgccgaatta ccgcttttc tcacagtgcc actggtcttc    7800
acggcgattg cctatccgat gatcggactg cgggccggag tgctgcactt cttcaactgc    7860
ctggcgctgg tcactctggt ggccaatgtg tcaacgtcct tcggatatct aatatcctgc    7920
gccagctcct cgacctcgat ggcgctgtct gtgggtccgc cggttatcat accattcctg    7980
```

```
ctctttggcg gcttcttctt gaactcgggc tcggtgccag tatacctcaa atggttgtcg    8040
tacctctcat ggttccgtta cgccaacgag ggtctgctga ttaaccaatg ggcggacgtg    8100
gagccgggcg aaattagctg cacatcgtcg aacaccacgt gccccagttc gggcaaggtc    8160
atcctggaga cgcttaactt ctccgccgcc gatctgccgc tggactacgt gggtctggcc    8220
attctcatcg tgagcttccg ggtgctcgca tatctggctc taagacttcg ggcccgacgc    8280
aaggagtaga aggtaagtag cggccgcacg taagggttaa tgttttcaaa aaaaaattcg    8340
tccgcacaca accttcctc tcaacaagca aacgtgcact gaatttaagt gtatacttcg    8400
```

-continued

```
attgaagcat ttatcagggt tattgtctca tgagcggata catatttgaa tgtatttaga    10380
aaaataaaca aatagggtt ccgcgcacat tccccgaaa agtgccacct gacgtctaag    10440
aaaccattat tatcatgaca ttaacctata aaaataggcg tatcacgagg ccctttcgtc    10500
tcgcgcgttt cggtgatgac ggtgaaaacc tctgacacat gcagctcccg gagacggtca    10560
cagcttgtct gtaagcggat gccgggagca gacaagcccg tcaggcgcg tcagcgggtg     10620 ttggcgggtg tcgggctgg cttaactatg cggcatcaga gcagattgta ctgagagtgc    10680
accatatgcg gtgtgaaata ccgcaccgaa tcgcgcggaa ctaacgacag tcgctccaag    10740
gtcgtcgaac aaaaggtgaa tgtgttgcgg agagcgggtg ggagacagcg aaagagcaac    10800
tacgaaacgt ggtgtggtgg aggtgaatta tgaagagggc gcgcgatttg aaaagtatgt    10860
atataaaaaa tatatcccgg tgttttatgt agcgataaac gagttttga tgtaaggtat     10920 gcaggtgtgt aagtcttttg gttagaagac aaatccaaag tctacttgtg gggatgttcg    10980 aagggaaat acttgtattc tataggtcat atcttgtttt tattggcaca aatataatta    11040
cattagcttt ttgaggggc aataaacagt aaacacgatg gtaataatgg taaaaaaaa     11100 aacaagcagt tatttcggat atatgtcggc tactccttgc gtcgggcccg aagtcttaga    11160
gccagatatg cgagcacccg gaagctcacg atgagaatgg ccagac                   11206
```

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: 5'P end of
      vector, splice acceptor site

<400> SEQUENCE: 2

```
tttgcgagta cgcaaagctc tttctcttac ag                                  32
```

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: stop-start
      seq., Gal4 gene

<400> SEQUENCE: 3

```
gtcgaattga tgtgatggat ccaatgaagc t                                   31
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: mini-white
      gene

<400> SEQUENCE: 4

```
agacttcggg cccgacgcaa ggagtagaag                                     30
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: splice
      donor site, 3'P end of GT vector

<400> SEQUENCE: 5

-continued

```
gtaagtagcg gccgcacgta agggttaatg                              30

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: anterior
      open cDNA exon 1

<400> SEQUENCE: 6
cagtacgtaa ccacagtgca cagtggagca aacag                        35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: anterior
      open cDNA exon 2

<400> SEQUENCE: 7
ataacaccgc ttaaaagcaa ttccagtggc ttccac                       36
```